United States Patent
Bouquet

(10) Patent No.: US 8,640,573 B2
(45) Date of Patent: Feb. 4, 2014

(54) RATCHET WRENCH

(75) Inventor: Joël Bouquet, Solothurn (CH)

(73) Assignee: Stryker Trauma SA (CH)

(*) Notice: Subject to any disclaimer, the term of this patent is extended or adjusted under 35 U.S.C. 154(b) by 246 days.

(21) Appl. No.: 13/215,466

(22) Filed: Aug. 23, 2011

(65) Prior Publication Data
US 2012/0055289 A1    Mar. 8, 2012

(30) Foreign Application Priority Data
Sep. 3, 2010    (EP) .................................... 10175237

(51) Int. Cl.
*B25B 13/00* (2006.01)
*B25B 13/46* (2006.01)
*B25B 13/04* (2006.01)

(52) U.S. Cl.
CPC ............... *B25B 13/00* (2013.01); *B25B 13/46* (2013.01); *B25B 13/463* (2013.01)
USPC .................................................. 81/61; 81/58

(58) Field of Classification Search
USPC ......................... 81/58.2, 60, 61, 58
See application file for complete search history.

(56) References Cited

U.S. PATENT DOCUMENTS

| | | | |
|---|---|---|---|
| 915,446 A * | 3/1909 | Kearnes | 81/63 |
| 1,119,900 A | 12/1914 | Vacarezza | |
| 1,513,212 A | 10/1924 | Beale | |
| 1,611,315 A * | 12/1926 | Miller | 81/125 |
| 1,615,497 A | 1/1927 | Woods | |
| 2,058,855 A * | 10/1936 | Chapman | 81/31 |
| 2,500,835 A | 3/1950 | Lang | |
| 2,697,371 A | 12/1954 | Hyman | |
| 2,711,112 A | 6/1955 | Durand | |
| 3,742,788 A | 7/1973 | Priest | |
| 3,921,475 A | 11/1975 | Evans | |
| 3,921,476 A | 11/1975 | Evans | |
| 3,967,514 A | 7/1976 | Deutch | |
| 4,592,255 A | 6/1986 | Mayer | |
| 4,862,775 A * | 9/1989 | Chow | 81/63.2 |
| 5,230,263 A | 7/1993 | Kwaka | |
| 5,551,322 A | 9/1996 | Mikic et al. | |
| 5,582,082 A | 12/1996 | Gajo | |
| 5,878,636 A * | 3/1999 | Baker | 81/119 |
| 5,878,698 A | 3/1999 | Lyell | |
| 5,988,022 A | 11/1999 | Wang | |
| 6,148,694 A * | 11/2000 | Spirer | 81/57.3 |
| D437,536 S * | 2/2001 | Macor | D8/28 |
| D437,638 S | 2/2001 | Harwell, IV | |

(Continued)

OTHER PUBLICATIONS

EP 10 17 5237 Search report dated Feb. 23, 2011.

*Primary Examiner* — David B Thomas
(74) *Attorney, Agent, or Firm* — Lerner, David, Littenberg, Krumholz & Mentlik, LLP

(57) ABSTRACT

A ratchet wrench for use in connection with medical instruments comprises a handle and a drive element which is rotatable around an axis (M) with respect to the handle. The wrench is adapted to tighten or loosen a respective element and a ratchet mechanism which is in connection with the drive element and which permits movement with respect to the handle in a first direction of rotation (R1) and blocks movement in the other direction of rotation (R2). The handle comprises a flat arm, wherein the ratchet mechanism is arranged on a bearing surface of the flat arm, and wherein the drive element extends through an opening in the flat arm in which opening the drive element is rotatably arranged.

23 Claims, 2 Drawing Sheets

(56) References Cited

U.S. PATENT DOCUMENTS

| | | |
|---|---|---|
| 6,260,447 B1 * | 7/2001 | Hutt ................................ 81/63 |
| 6,269,715 B1 | 8/2001 | Cagny |
| 6,318,216 B1 * | 11/2001 | Eggert et al. .................... 81/61 |
| 6,443,038 B2 * | 9/2002 | Hsieh ............................. 81/119 |
| 6,446,530 B1 * | 9/2002 | Chang ............................. 81/60 |
| 6,449,038 B1 | 9/2002 | Stolze |
| 6,516,689 B1 | 2/2003 | Bates |
| 6,530,296 B1 * | 3/2003 | Liao ................................ 81/60 |
| 6,530,298 B1 | 3/2003 | Steffe |
| 6,769,329 B1 | 8/2004 | Gao et al. |
| 6,993,997 B1 | 2/2006 | Marro |
| 2002/0011136 A1 * | 1/2002 | Eggert et al. ................. 81/125.1 |
| 2004/0250658 A1 * | 12/2004 | Liao ............................... 81/58.2 |
| 2005/0252347 A1 | 11/2005 | Austin et al. |
| 2006/0065083 A1 * | 3/2006 | Liao ............................... 81/438 |
| 2011/0179912 A1 * | 7/2011 | Lin ................................ 81/60 |

\* cited by examiner

RATCHET WRENCH

BACKGROUND OF THE INVENTION

The present invention relates to a coupling ratchet wrench or socket wrench, in particular for use in surgeries.

Ratchet wrenches are frequently used in surgeries in order to tighten screws of any kind. One example is the use of a ratchet wrench in order to tighten bolts and nuts in connection with an external fixator. Such ratchet wrenches are tools which are used several times and have therefore to be cleaned and sterilized between two uses.

A ratchet wrench usually comprises a ratchet mechanism which allows a nut to be tightened or loosened with a reciprocating motion without requiring that the wrench be removed and refitted after each turn.

From known ratchet wrenches usually the drawback arises that the ratchet mechanism is usually arranged within a housing and that cleaning of the ratchet mechanism is not very effective. With other words, the ratchet mechanism is encapsulated by the housing. Thereby bacteria and other impurities remain in the ratchet mechanism which may lead to bacterial strains. Bacteria and impurities can lead to complications such as infections etc. of the patient during surgeries.

Furthermore the known ratchet wrenches usually comprises an actuation element to change the direction of the ratchet mechanism. The actuation element usually also provides spaces in which growth of bacterial strains becomes possible.

BRIEF SUMMARY OF THE INVENTION

It is therefore an object of the present invention to provide a ratchet wrench which does not have the drawbacks of prior art. In particular the ratchet wrench shall be provided such that cleaning and sterilisation becomes more effective.

Such an object is achieved by a ratchet wrench for use in connection with medical instruments which comprises a handle, a drive element which is rotatable around an axis with respect to the handle and which is adapted to tighten or loosen a respective element. A ratchet mechanism is in connection with said drive element and which permits movement with respect to the handle in a first direction of rotation and blocks movement in the other direction of rotation. The handle comprises a flat arm, wherein the ratchet mechanism is arranged on a bearing surface of the flat arm, and wherein said drive element extends through an opening in said flat arm in which opening the drive element is rotatably arranged. The ratchet mechanism is thereby in connection with the flat arm. Due to the shape of the handle and the arrangement of the ratchet mechanism on the handle a structure results which is cleanable in a very easy manner.

Preferably the handle comprises two flat arms which are arranged at a distance from each other, whereas an interior space is provided between the arms, in which interior space the ratchet mechanism is arranged. Preferably the interior space remains apart from the flat arms uncovered so that access to the interior space is provided from outside. The interior space is provided such that access is provided from the outside to allow effective cleaning. Preferably the drive element is a socket or a universal joint adapted to receive a drive fitting.

Preferably the ratchet mechanism comprises a pivoting spring-loaded finger which engages into a gear element which is in a fixed connection with the drive element or which is part of the drive element. The spring-loaded finger and the gear element provide a ratchet mechanism with very few parts thus allowing also advantageous cleaning properties.

Preferably the spring-loaded finger is in connection with said arm(s) by means of a bolt, wherein the spring-loaded finger pivots around said bolt which is in a fixed connection with the arm(s). Alternatively the spring-loaded finger is in connection with the arm(s) by means of a bolt, wherein the spring-loaded finger is in a fixed connection with said bolt, and wherein the bolt is pivotable with respect to the arm(s). Preferably the spring-loaded finger is in connection with a leaf spring that extends with one end into a receptacle or an opening within the finger and is in connection with the other end with a bolt which is also in connection with the arm(s).

Other aspects of the invention are provided by a ratchet wrench for use in connection with medical instruments comprising a handle having a flat arm providing a bearing surface and having an opening extending through the flat arm. A drive element is rotatable around an axis with respect to the handle and which is adapted to tighten or loosen a respective element. The drive element extends through the opening in the flat arm in which opening the drive element is rotatably arranged. A ratchet mechanism is provided which is in connection with the drive element and which permits movement with respect to the handle in a first direction of rotation and blocks movement in the other direction of rotation. The ratchet mechanism is arranged on a bearing surface of the flat arm. The handle comprises two flat arms which are arranged at a distance from each other. An interior space is provided between the arms, in which interior space the ratchet mechanism is arranged. The interior space extends along the whole length of the flat arms. The interior space remains apart from the flat arms uncovered so that access to the interior space is provided from outside. The drive element may be a socket or a universal joint adapted to receive a drive fitting. The ratchet mechanism may comprise a pivoting spring-loaded finger which engages into a gear element which is in a fixed connection with the drive element. The ratchet mechanism comprises a pivoting spring-loaded finger which engages into a gear element which is part of the drive element wherein the spring-loaded finger is in connection with the arm(s) by means of a bolt. The spring-loaded finger pivots around the bolt which is in a fixed connection with the arm(s). The bolt may be pivotable with respect to the arm(s). The spring-loaded finger is in connection with a leaf spring that extends with one end into a receptacle within the finger and is in connection at the other end with a bolt which is also in connection with the arm(s). The spring-loaded finger is provided with a spring force in any of its positions such that the finger will always be forced to be in contact with the gear element. The flat arm may comprise at least one or a plurality of openings which provide better access to the interior space. Preferably the drive element extends along a central axis and is accessible from both directions of the middle axis so that the ratchet wrench can be used to loosen as well as to tighten a nut.

Other aspects of the invention are provided by a ratchet wrench for use in connection with medical instruments including a handle comprised of first and second plates defining a space therebetween. An opening extends through the first and second plates adjacent a first end of the handle. A drive element is mounted in the opening, the drive element including a ratchet mechanism extending into the space between the first and second plates. The ratchet mechanism has a plurality of teeth and a locking finger is rotatably mounted in the space between the first and second plates for rotation about a pivot point. The locking finger has a tip on a first side of the pivot point engaging a tooth of the plurality of teeth on the ratchet mechanism. A spring element is provided which has a first end engaging the finger at a point thereon on a second side of the pivot point, a second end of the spring element is fixed with respect to the first and second plates at a second end of the handle. The interior space extends along the whole length of said flat arms and the interior space remains apart from the flat arms uncovered so that access to the interior space is provided from the outside. The drive element may be a socket or a universal joint adapted to receive a drive fitting. The spring-loaded finger is in connection with said arm(s) by means of a bolt, wherein the spring-loaded finger pivots around the bolt which is in a fixed connection with the arm(s). The spring-loaded finger may be in connection with said arm(s) by means of a bolt and the spring-loaded finger is in a fixed connection with the bolt, and wherein said bolt is pivotable with respect to the arm(s). The spring-loaded finger may be in connection with a leaf spring that extends with one spring end in a receptacle within the finger and is in connection at the other end with a bolt which is also in connection with the arm(s).

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 1:
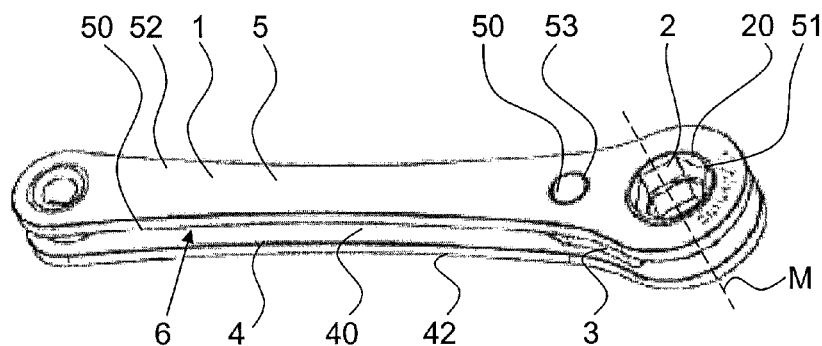
FIG. 1 is a perspective view of a ratchet wrench.

In the figures a ratchet wrench for use with medical instruments is shown. The medical ratchet wrench is in particular used in sterile environments such as in a operating theatre.

The ratchet wrench comprises a handle 1, a drive element 2 which is rotatable around a central axis M with respect to the handle 1 and which is adapted to tight or loosen a respective element, such as a screw or a nut and a ratchet mechanism 3 which is in connection with said drive element 2. The ratchet mechanism permits movement in a first direction of rotation R1 and blocks movement in the other direction of rotation R2. Hence, if the user wants to tighten a screw it is not necessary to make a full rotation. The user may make a rotation about a part of a full rotation, thereby the relative movement between the drive element 2 is blocked and the drive element 2 acts onto screw and upon a movement in the other direction the ratchet mechanism permits movement such that drive element 2 is not rotated.

The handle 1 comprises a flat arm or plate 4. In the present embodiment two flat arms or plates 4, 5 are shown, but it may also be possible to provide the handle with only one flat arm or plate 4. The flat arm 4 serves as bearing element for the other parts of the ratchet wrench and as handle for the user. Preferably the flat arm can be provided by cutting or punching the arm out of a metal sheet. The term flat shaped is to be understood that thickness of the arm is thin compared to its length and width.

Flat arms or plates 4, 5 respectively comprises inwardly facing bearing surfaces 40, 50 and an outer surface 42, 52. the bearing surface 40, 50 is thereby preferably parallel to the outer surface 42, 52.

The bearing surface 40, 50 serves to mount the ratchet mechanism 3 and also the drive element 2. Thereby the ratchet mechanism 3 is arranged on a bearing surface 40 of flat arm 4 and drive element 2 extends through an opening 41, 51 in flat arms 4, 5. The drive element 2 is rotatably mounted in openings 41, 51.

Figure 2:
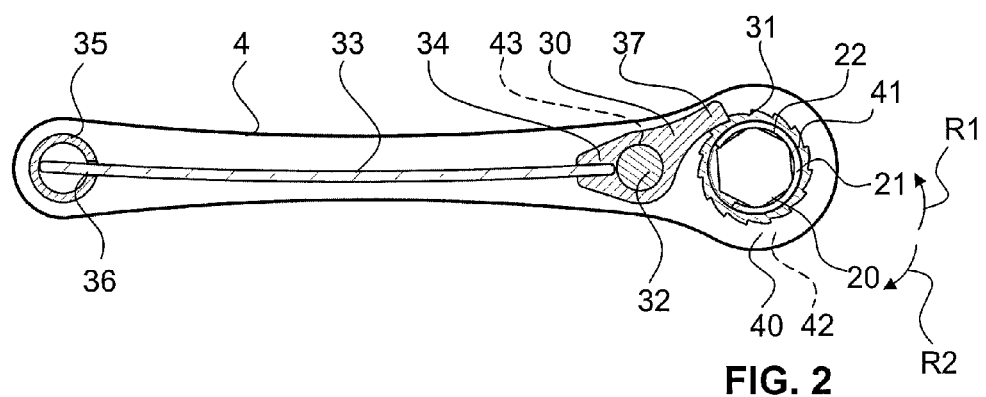
FIG. 2 is a section view of FIG. 1 showing the ratchet mechanism.
Figure 4:
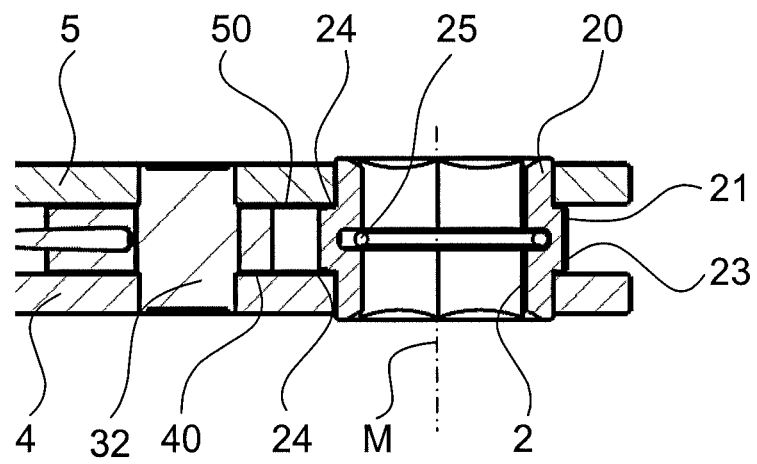
FIG. 4 is a section view of the front portion of the ratchet mechanism along a plane containing axis M.

Referring to FIGS. 2 and 4 drive element 2 is shown as a socket element 20 which extends along a middle axis M. The socket element 20 comprises an outer surface 21 which is in an engagement with openings 41, 51 and an opening 22. Opening 22 may have a hexagonal cross-section and be used to tighten or loosen a nut with a corresponding cross section. The outer surface 21 has, in its region in which the drive element 2 extends into the respective opening 41, 51, a diameter so that the drive element 2 can be rotated with respect to the opening 41, 51 or the flat arm 4, 5 respectively.

In FIG. 4 it can be recognized that the outer surface 21 of the socket element 20 comprises a circumferential rim 23. The circumferential rim 23 provides two bearing surfaces 24 which engage with the bearing surfaces 40 and 50. Thereby the socket element 20 is secured by means of the rim 23 or the surfaces 24 against a movement along middle axis M. In FIG. 4 it can also be seen that the socket element 20 may comprise a circlip 25 with which a thumbwheel or another tool can be secured.

Alternatively the drive element 2 can also comprise a universal joint on which a drive fitting such as a thumbwheel or hex socket can be added. The arrangement of a universal joint allows more flexibility since different drive elements can be used.

As mentioned above preferably two flat arms 4, 5 are arranged at a distance to each other. This means that the handle 1 comprises two flat arms 4, 5. Between the two flat arms there is provided an interior space 6. Within interior space 6 the ratchet mechanism 3 is arranged. It has to be noted that apart from the two flat arms 4, 5 the interior space 6 is fully accessible from the outside which means that there is no further cover which covers the interior space 6. In other words it may also be said that the ratchet mechanism 3 is encapsulated. This has the advantage that the interior space 6 is easily accessible for cleaning and sterilization purposes. Hence the risk that bacteria remains in the wrench after a cleaning and/or sterilization process is rather low compared to the wrenches as known from prior art.

Additionally it may also be possible to add several openings which extend through the respective arm 4, 5 from the outer surface 42, 52 to the bearing surface 40, 50 in order to provide even better access to the interior space. It is also possible to add such openings only in one of the arms in order to enhance stability in case larger forces are required.

In case only one flat arm 4 is arranged, the region above the bearing surface 40 is also considered as interior space 6, wherein said interior space extends up to the height of the drive element 2. In this embodiment even better access is provided to said interior space.

With regard to FIG. 2 the ratchet mechanism 3 will now be explained in the following. The ratchet mechanism 3 comprises a pivoting spring-loaded finger 30 which engages into a gear or ratchet element 31 which is in a fixed connection with the drive element 2 or which is part of the drive element 2. Preferably the gear or ratchet element 31 encompasses the drive element 2 around its whole perimeter.

The pivoting spring-loaded finger 30 is in connection with a bolt or pivot pin 32 that is in an engagement with the two arms 4, 5 or with the single arm 4. The spring-loaded finger is thereby pivotable about the middle axis which extends through the bolt or pin 32 in parallel direction to middle axis M. In one embodiment the finger 30 is pivotable with respect to the bolt 32 which is then in a fixed connection with the arm 4, 5. Preferably the bolt is then connected via a press-fit with an opening 43, 53 that is arranged in the respective arm 4, 5. Alternatively a welded connection is also possible.

In a further embodiment the finger 30 is in a fixed connection with the bolt 32 which then is rotatable with respect to the arm 4, 5.

Figure 3:
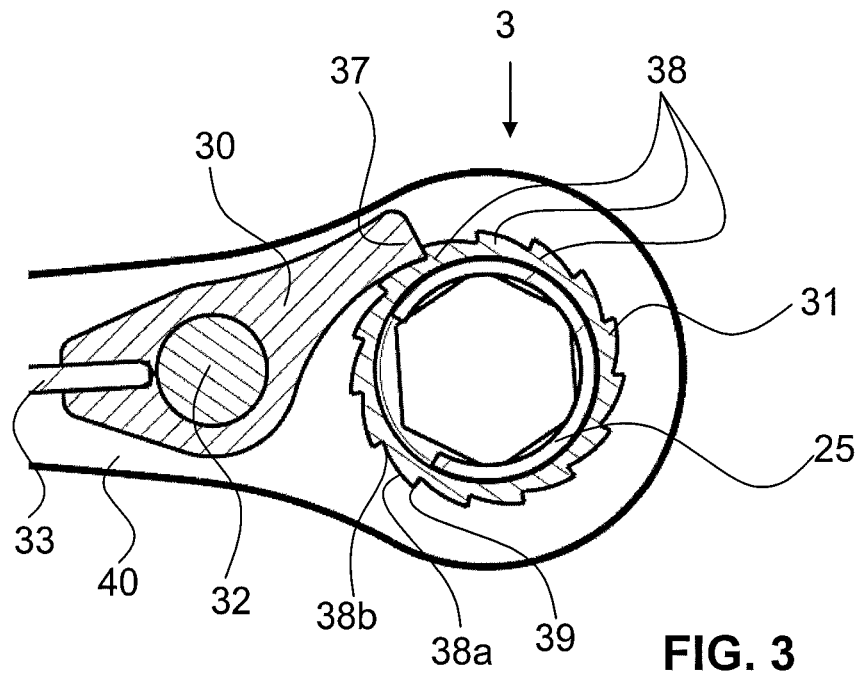
FIG. 3 is a detailed view of the ratchet mechanism.

FIG. 3 shows a detailed view of the ratchet mechanism. The finger 30 engages with its tip 37 into the gear or ratchet element 31. The gear element 31 comprises a plurality of teeth 38 which are arranged around the perimeter of the gear element 31. The teeth 38 are formed asymmetrical. Thereby each tooth has a moderate slope 38a on one edge and a much steeper slope 38b on the other edge. Starting from the intersection point 39 between the moderate slope 38a and the steep slope 38b a rotation is permitted in direction of the moderate slope 38a, as the spring loaded finger 30 will be actuated due to the angular situation of the slope 38a. In the opposite direction, meaning towards the steep slope a rotation will be blocked or not permitted, since the spring-loaded finger 30 remains in its position.

The ratchet mechanism 3 comprises in the present embodiment a leaf spring 33 which serves to provide the finger 30 as spring-loaded finger. The leaf spring 33 extends with one end into a receptacle 34 that is arranged within finger on one side of the pivot point angularly offset from the side of the pivot point having tip 37. With the other end the leaf spring 33 extends into or through a receptacle 36 which is arranged in a bolt 35 that is in connection with the flat arm 4 and with the flat arm 5, if the latter is present. Thereby the leaf spring 33 will be loaded by means of a bending load since the leaf spring will be flexed. If flat arm 4 as well as flat arm 5 are present, leaf spring 33 is arranged in the interior space 6 between the two arms 4, 5. Preferably leaf spring 33 extends through substantially the whole length of the handle 1.

With regard to the leaf spring 33 it has to be noted that it is very advantageous, if the leaf spring is pre-tensioned such that in the position in which tip 37 of finger 30 engages into the gear element 31 a force will be provided pushing the finger 30 against the gear element 31. Pre-tensioning of the leaf spring 33 is achieved by arranging the respectable 36 and the receptacle 34 slightly angular to each other.

Although the leaf spring 33 is very advantageous concerning the cleaning and sterilization process it has to be noted that any other spring which provides a radial force around the bolt 32 or the axis of rotation of the spring-loaded finger 30, respectively, may be used.

The bolts 32 and 35 not only serve as bearing elements for the finger 32, but also as connection elements to connect the flat arm 4 with the flat arm 5. Preferably the bolts 32 and 35 are in connection with the flat arm 4 and/or the flat arm 5 by means of a press-fit or a welded connection. In order to maintain the distance between the flat arms 4, 5 the bolts 32, are optionally provided with different diameters, whereby the diameter in that section which extends through the interior space 6 is larger that the diameter extending into the respective opening in the flat arm 4, 5.

The bolt 32 can also be provided with a colour code which shows in which direction such as tightening or loosing direction the wrench is to be used.

As mentioned above the ratchet mechanism 3 allows that in one direction rotation of the drive element 2 is permitted and that in the other direction rotation is not permitted or blocked. The direction of the non-permitted or blocked rotation is therefore used to drive or actuate a screw. The ratchet wrench may be used to loosen and as well as tighten a screw. For that reason it is provided symmetrical which means that in case the flat arm 4 is directed towards the screw the wrench may be used to loosen a screw and in case the flat arm 5 is directed towards the screw the same wrench may be used to tighten a screw. This means that the wrench may be used to tighten and to loosen a screw, whereby the wrench has to be turned around the axis in which the leaf spring 33 extends. For that reason the same ratchet wrench may be used to loosen as well as to tighten a screw whereas it has to be turned about its own axis.

In order to provide this feature in a simple manner, the drive element 2 preferably extends along a middle axis M and is accessible from both directions of said middle axis M so that the ratchet wrench can be used to loosen as well as to tighten a nut by flipping the wrench over.

Preferably all of the elements as mentioned above are made out of metal. In particular stainless steel or titanium.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A ratchet wrench for use in connection with medical instruments comprising:
    a longitudinally extending handle comprised of first and second plates, the first and second plates being spaced apart and extending in parallel defining an interior space between the first and second plates, the interior space having open sides extending between peripheries of the first and second plates, and exposing the interior space of the handle, an opening extending through the first and second plates adjacent a first end of the handle;
    a drive element mounted in the opening, the drive element including a ratchet mechanism extending into the space between the first and second plates, the ratchet mechanism having a plurality of teeth;
    a locking finger rotatably mounted in the interior space between the first and second plates for rotation about a pivot point, the locking finger having a tip on a first side of the pivot point engaging a tooth of the plurality of teeth on the ratchet mechanism; and
    an elongated leaf spring having a first end engaging the finger at a point thereon on a second side of the pivot point, a second end of the spring element coupled to a bolt fixed with respect to the first and second plates at a second end of the handle, the spring exposed to the open sides of the wrench.

2. The ratchet wrench according to claim 1, wherein said interior space extends along a longitudinal extent of said first and second plates.

3. The ratchet wrench according to claim 1, wherein said drive element is a socket or a universal joint adapted to receive a drive fitting.

4. The ratchet wrench according to claim 1, wherein the spring-loaded finger is in connection with said first and second plates by means of a pin, wherein the spring-loaded finger pivots around said pin which is in a fixed connection with said first and second plates.

5. The ratchet wrench according to claim 4, wherein the spring-loaded finger is in connection with said first and second plates by means of a pin, wherein the spring-loaded finger is in a fixed connection with said pin, and wherein said pin is pivotable with respect to said first and second plates.

6. The ratchet wrench according to claim 1, wherein the spring-loaded finger is in connection with the leaf spring that has a first end which extends into a receptacle within the finger and is in connection with the other end with a bolt which extends between and is in connection with said first and second plates.

7. A ratchet wrench for use in connection with medical instruments comprising:
- a longitudinally extending handle comprising first and second flat plates and having an aligned opening extending through said first and second plates at a first end thereof, the first and second flat plates being spaced apart and extending in parallel, an interior space between the first and second plates having open sides defined by peripheries of the first and second plates,
- a drive element, which is rotatable around an axis with respect to the handle and which is adapted to tighten or loosen a respective element, wherein said drive element extends through said opening in said flat first and second plate in which opening said drive element is rotatably mounted,
- a ratchet mechanism including a spring-loaded finger which is in connection with said drive element and which permits movement with respect to the handle in a first direction of rotation and blocks movement in a second opposite direction of rotation, wherein said ratchet mechanism is arranged in the interior space between the first and second plates, and
- a bolt extending between the first and second plates at a second end of the handle and a leaf spring coupled to the bolt at a first end and to the finger at a second end of the leaf spring, the leaf spring exposed to the open sides of the handle.

8. The ratchet wrench according to claim 7, wherein said drive element is a socket or a universal joint adapted to receive a drive fitting.

9. The ratchet wrench according to claim 7, wherein the ratchet mechanism pivoting spring-loaded finger engages into a gear element which is in a fixed connection with the drive element.

10. The ratchet wrench according to claim 7, wherein the ratchet mechanism pivoting spring-loaded finger which into a gear element which is part of the drive element.

11. The ratchet wrench according to claim 10, wherein the spring-loaded finger is in connection with said first and second plates by means of a pin, wherein the spring-loaded finger pivots around said pin which pin is in a fixed connection with said first and second plates.

12. The ratchet wrench according to claim 10, wherein the spring-loaded finger is in connection with said first and second plates by means of a pin, wherein the spring-loaded finger is in a fixed connection with said pin, and wherein said pin is pivotable with respect to said first and second plates.

13. The ratchet wrench according to claim 12, wherein the spring-loaded finger is in connection with the leaf spring second end extending into a receptacle within the finger and is in connection at the first end with the bolt, which bolt is in connection with said first and second plates.

14. The ratchet wrench according to claim 10, wherein the spring-loaded finger is provided with a spring force from the leaf spring in any of its positions such that the finger will always be forced to be in contact with the gear element.

15. The ratchet wrench according to claim 7, wherein the first and second plates flat comprises at least one or a plurality of opening providing better access to the interior space.

16. The ratchet wrench according to claim 7, wherein the drive element extends along a central axis and is accessible from both directions of said central axis so that the ratchet wrench can be used to loosen as well as to tighten a nut, the central axis being perpendicular to a plane of the first and second parallel plates.

17. A ratchet wrench for use in connection with medical instruments comprising:
- a handle, a drive element which is rotatable around an axis with respect to the handle and which is adapted to tighten or loosen a respective element and a ratchet mechanism which is in connection with said drive element and which permits movement with respect to the handle in a first direction of rotation and blocks movement in a second direction of rotation, wherein said handle comprises a flat arm, wherein said ratchet mechanism is arranged on a bearing surface of said flat arm and wherein said drive element extends through an opening in said flat arm in which opening said drive element is rotatably arranged;
- wherein the handle comprises two flat arms which are arranged at a distance from each other, whereas an interior space is provided between said arms in which interior space said ratchet mechanism is arranged;
- wherein said interior space remains apart from said flat arms uncovered so that access to said interior space is provided from outside;
- wherein the ratchet mechanism comprises a pivoting spring-loaded finger which engages into a gear element which is in a fixed connection with the drive element or which is part of the drive element, and
- wherein the spring-loaded finger is in connection with a leaf spring that extends with a first end into a receptacle within the finger and is in connection with at a second end with a bolt which is also in connection with said arms.

18. The ratchet wrench according to claim 17, wherein said drive element is a socket or a universal joint adapted to receive a drive fitting.

19. The ratchet according to claim 17, wherein the spring-loaded finger is in connection with said arms by means of a bolt, wherein the spring-loaded finger pivots around said bolt which is in a fixed connection with said arms.

20. The ratchet according to claim 17, wherein the spring-loaded finger is in connection with said arms by means of a bolt, wherein the spring-loaded finger is in a fixed connection with said bolt, and wherein said bolt is pivotable with respect to said arms.

21. The ratchet wrench according to claim 17, wherein the spring-loaded finger is provided with a spring force in any of its positions such that the finger will always be forced to be in contact with the gear element.

22. The ratchet wrench according to claim 17, wherein at least one of the flat arms comprises at least one opening which provides better access to the interior space.

23. The ratchet wrench according to claim 17, wherein the drive element extends along a central axis and is accessible from both directions of said central axis so that the ratchet wrench can be used to loosen as well as tighten a nut.

* * * * *